US012667596B2

(12) United States Patent (10) Patent No.: US 12,667,596 B2

Huang et al. (45) Date of Patent: Jun. 30, 2026

(54) METHOD FOR PROMOTING BONE HEALING

(71) Applicant: SYNBIO TECH INC., Kaohsiung City (TW)

(72) Inventors: Yu-Tzu Huang, Taipei City (TW); Hsuan Chou, Taipei City (TW); Jyun-Sian Wu, Taoyuan City (TW); Chia-Chia Lee, Kaohsiung City (TW); Han-Yin Hsu, Kaohsiung City (TW)

(73) Assignee: SYNBIO TECH INC., Kaohsiung City (TW)

( * ) Notice: Subject to any disclaimer, the term of this patent is extended or adjusted under 35 U.S.C. 154(b) by 994 days.

(21) Appl. No.: 17/915,436

(22) PCT Filed: Apr. 21, 2022

(86) PCT No.: PCT/CN2022/088243

§ 371 (c)(1),
(2) Date: Sep. 28, 2022

(87) PCT Pub. No.: WO2022/223005

PCT Pub. Date: Oct. 27, 2022

(65) Prior Publication Data

US 2023/0139904 A1 May 4, 2023

Related U.S. Application Data

(60) Provisional application No. 63/178,952, filed on Apr. 23, 2021.

(51) Int. Cl.
*A61K 35/747* (2015.01)
*A23L 33/135* (2016.01)
*A61K 35/00* (2006.01)

(52) U.S. Cl.
CPC .......... *A61K 35/747* (2013.01); *A23L 33/135* (2016.08); *A23V 2400/169* (2023.08); *A61K 2035/115* (2013.01)

(58) Field of Classification Search
CPC ................ A61K 35/747; A23L 33/135; A23V 2400/169; A61P 19/00; A61P 19/10; A61P 19/08
See application file for complete search history.

(56) References Cited

FOREIGN PATENT DOCUMENTS

TW 583388 B 5/2017

OTHER PUBLICATIONS

Huang: Effect of Lactobacillus Plantarum TWK10 on Improving Endurance Performance in Humans, Jun. 30, 2018 (Jun. 30, 2018), Chinese Journal of Physiology (Year: 2018).*
International Search Report issued in PCT/CN2022/088243, Jul. 26, 2022 (2 pages).

* cited by examiner

*Primary Examiner* — Louise W Humphrey
*Assistant Examiner* — Alexander M Duryee
(74) *Attorney, Agent, or Firm* — HSML P.C.

(57) ABSTRACT

A method for promoting bone healing in a subject includes administering to the subject in need thereof a composition including *Lactobacillus plantarum* TWK10 deposited at China General Microbiological Culture Collection Center with an accession number CGMCC No. 13008. The composition can effectively promote activation and generation of osteoblasts, and bone maturation.

3 Claims, 6 Drawing Sheets

METHOD FOR PROMOTING BONE HEALING

FIELD

The present disclosure relates to use of *Lactobacillus plantarum* TWK10 (CGMCC No. 13008) for promoting bone healing in a subject.

BACKGROUND

When a bone is damaged (e.g., fissure fracture, also known as bone fracture) by an external force, healing mainly occurs through a patient's own bone healing ability. However, when the extent of injury is severe and causes bone defects, such as segmental fractures, bone implantation is further required to facilitate bone healing. In order to introduce an implant into a bone, it is necessary sometimes to first perform bone destruction on a patient. However, the ability of the bone to heal decreases relatively with the extent of bone damage and increased age. Therefore, related researchers in the field are committed to develop measures that can effectively promote bone healing.

TW 1583388 B discloses use of *Lactobacillus plantarum* BCRC 910734 to increase exercise performance and decrease fatigue. In the Examples section of such patent document, 6-week-old mice, after taking *Lactobacillus plantarum*. BCRC 910734 for 6 weeks, were demonstrated to have a greater forelimb grip strength and can swam for longer time period, as well as a significant decrease in concentrations of lactic acid and ammonia in the blood after exercise.

SUMMARY

An object of the present disclosure is to achieve the effect of bone healing by promoting activation and generation of osteoblasts, and bone maturation, which can alleviate at least one of the drawbacks of the prior arts.

In a first aspect, the present disclosure provides a method for promoting bone healing in a subject includes administering to the subject in need thereof a composition including *Lactobacillus plantarum* TWK10 (CGMCC No. 13008).

In a second aspect, the present disclosure provides use of *Lactobacillus plantarum* TWK10 (CGMCC No. 13008) in the manufacture of a composition for promoting bone healing in a subject.

In a third aspect, the present disclosure provides a composition for promoting bone healing in a subject, which includes *Lactobacillus plantarum* TWK10 (CGMCC No. 13008).

In a fourth aspect, the present disclosure provides use of *Lactobacillus* plantarum TWK10 (CGMCC No. 13008) for promoting bone healing in a subject.

BRIEF DESCRIPTION OF THE DRAWINGS

Other features and advantages of the present disclosure will become apparent in the following detailed description of the embodiments with reference to the accompanying drawings, of which.

DETAILED DESCRIPTION

Figure 1:
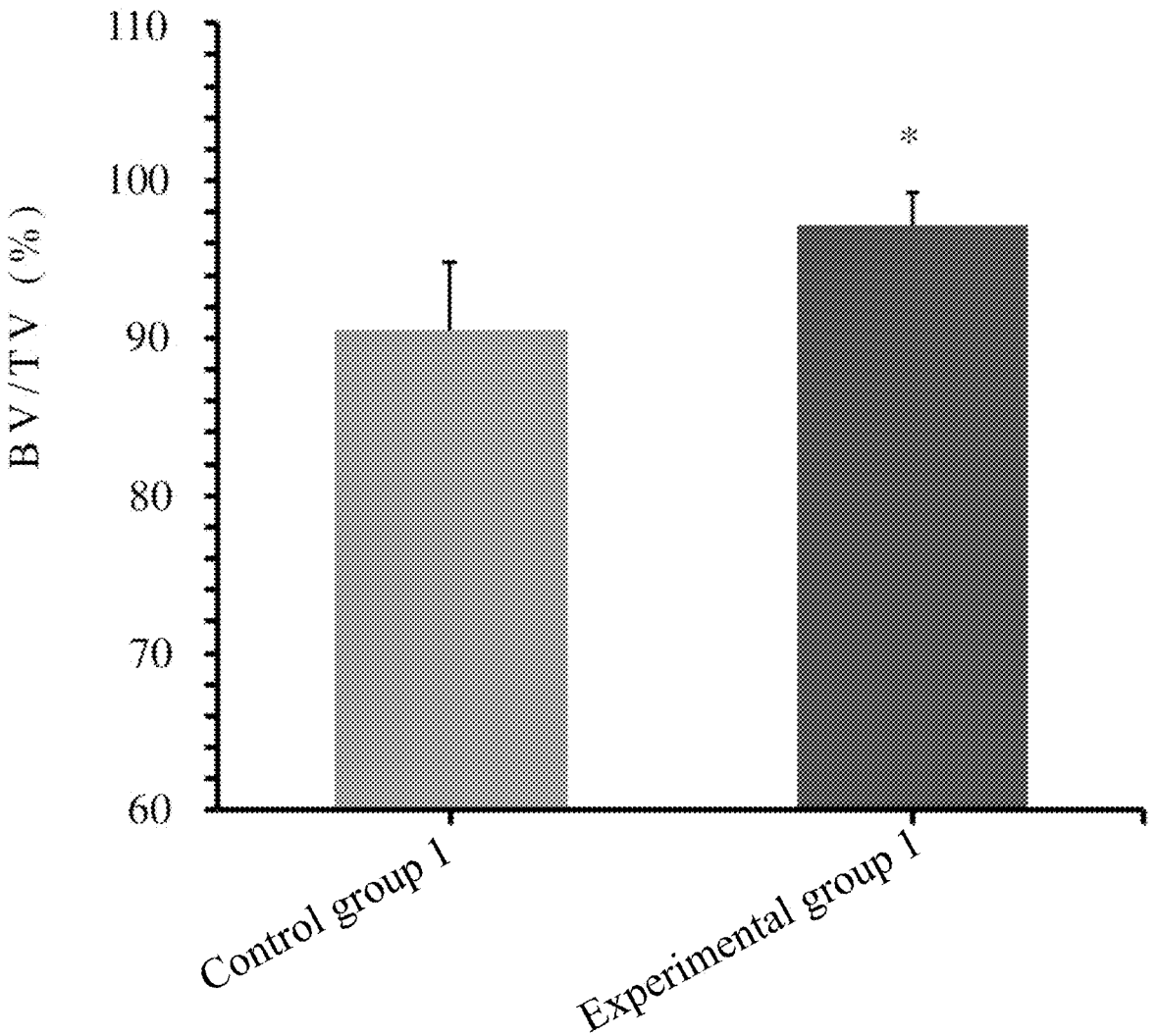
FIGS. 1 and 2 respectively show the bone volume fraction (BV/TV) (%) and bone mineral density (BMD) (g/mm$^3$) measured in femurs of the rats in control group 1 and experimental group 1 of Example 1, infra, in which the symbols "s" represents p<0.05 (compared with the control group 1)

It is to be understood that, if any prior art publication is referred to herein, such reference does not constitute an admission that the publication forms a part of the common general knowledge in the art, in Taiwan or any other country.

For the purpose of this specification, it will be clearly understood that the word "comprising" means "including but not limited to", and that the word "comprises" has a corresponding meaning.

Unless otherwise defined, all technical and scientific terms used herein have the meaning commonly understood by a person skilled in the art to which this disclosure belongs. One skilled in the art will recognize many methods and materials similar or equivalent to those described herein, which could be used in the practice of this disclosure. Indeed, this disclosure is in no way limited to the methods and materials described.

The present disclosure provides a composition including *Lactobacillus plantarum* TWK10 (CGMCC No. 13008) for promoting bone healing in a subject.

The present disclosure also provides use of *Lactobacillus plantarum* TWK10 (CGMCC No. 13008) in the manufacture of a composition for promoting bone healing in a subject. The present disclosure also provides a method for promoting bone healing in a subject which includes administering to the subject in need thereof a composition including *Lactobacillus plantarum* TWK10.

As used herein, the term "administering" and the term "administration" can be used interchangeably, and refers to introducing, providing or delivering an active ingredient to a subject by any suitable route to perform its intended function.

In addition, the present disclosure provides use of *Lactobacillus plantarum*. TWK10 for promoting bone healing in a subject.

According to the present disclosure, *Lactobacillus plantarum* TWK10 may be alive or dead, concentrated or non-concentrated, liquid, paste, semi-solid, or solid (e.g., pellet, fine granule or powder), and may be heat-inactivated, frozen, dried, or freeze-dried (e.g., in freeze-dried form or in spray/fluid bed dried form). In an exemplary embodiment, *Lactobacillus* plantarum TWK10 is in a freeze-dried powder form.

As used herein, the term "bone healing" and the term "bone repair" can be used interchangeably.

According to the present disclosure, the subject may have a bone fracture caused by one of the following: trauma;

congenital bone healing disorders, e.g., osteogenesis imperfecta; cancer, e.g., bone metastasis; and surgery, e.g., bone lengthening and limb lengthening procedures and tumor resection surgery, such as primary bone tumor resection and secondary bone cancer (also known as bone metastasis) resection.

According to the present disclosure, the bone fracture may include, but not limited to, simple fracture, open fracture, transverse fracture, fissure fracture (also known as longitudinal fracture), oblique fracture, spiral fracture, compression fracture, segmental fracture, communicated fracture, avulsion fracture, greenstick fracture, and dislocation fracture.

Alternatively, the subject may have osteonecrosis, e.g., osteonecrosis complicated by fractures, and ischemic osteonecrosis caused by osteomyelitis.

According to the present disclosure, the subject may have undergone a surgical intervention of bones, which may include, but is not limited to, bone replacement, e.g., replacement of hip and knee joints; and bone implantation, e.g., tooth implantation.

In certain embodiments, the subject does not have osteoporosis.

As used herein, the term "subject" refers to any mammals of interest, such as humans, monkeys, cows, sheep, horses, pigs, goats, dogs, cats, mice, and rats.

According to the present disclosure, the composition may be formulated into a food product using standard techniques well-known to those skilled in the art. For example, the composition may be directly added to an edible material, or may be used to prepare an intermediate composition (e.g., food additive or premix) suitable to be subsequently added to the edible material.

As used herein, the term "food product" refers to any article or substance that can be ingested into a body of a subject. Examples of the food product may include, but not limited to, fluid milk products, e.g., milk and concentrated milk; fermented milk, e.g., yogurt, sour milk and frozen yogurt; milk powder; ice cream; cream cheese; dry cheese; soybean milk; fermented soybean milk; vegetable-fruit juices; fruit juices, sports drinks; jelly; cookies; energy bars; health foods; animal feeds; and dietary supplements.

According to the present disclosure, the composition may be prepared in a form of a pharmaceutical composition.

According to the present disclosure, the pharmaceutical composition may be in a dosage form suitable for oral administration, parenteral administration or topical administration.

According to the present disclosure, the pharmaceutical composition may further include a pharmaceutically acceptable carrier that is widely used in pharmaceutical manufacturing technology. For example, the pharmaceutical acceptable carrier may include an agent selected from the group consisting of solvent, buffer, emulsifier, suspending agent, decomposer, disintegrating agent, dispersing agent, binding agent, excipient, stabilizing agent, chelating agent, diluent, gelling agent, preservative, wetting agent, lubricant, absorption delaying agent, liposome, and the like, and combinations thereof. The selection and amount of the agent are within the expertise and routine skills of those skilled in the art.

According to the present disclosure, the pharmaceutical composition may be formulated into a dosage form suitable for oral administration using techniques well-known to those skilled in the art.

Examples of the dosage form suitable for oral administration include, but not limited to, sterile powder, tablet, troche, lozenge, pellet, capsule, dispersible powder or granule, solution, suspension, drop, emulsion, syrup, elixir, slurry, and the like.

According to the present disclosure, the pharmaceutical composition may be formulated into a dosage form suitable for parenteral administration (including injection, e.g., sterile aqueous solution or dispersion) using techniques well-known to those skilled in the art, and administered by a route selected from the group consisting of intraperitoneal injection, intrapleural injection, intramuscular injection, intravenous injection, intraarterial injection, intraarticular injection, intrasynovial injection, intrathecal injection, intracranial injection, intraepidermal injection, subcutaneous injection, intradermal injection, intralesional injection, and sublingual administration.

According to the present disclosure, the pharmaceutical composition may be formulated as an external preparation suitable for topical application on the skin using techniques well-known to those skilled in the art. Examples of the external preparation suitable for topical application include, but not limited to, emulsion, gel, ointment, cream, patch, liniment, powder, aerosol, spray, lotion, serum, paste, foam, drop, suspension, salve, and bandage.

According to the present disclosure, the dosage and frequency of administration of *Lactobacillus plantarum* TWK10 will vary depending on severity of disease to be treated, route of administration, and age, physical condition and response of the subject to be treated. In general, *Lactobacillus plantarum* TWK10 may be administered parenterally, orally, or topically, in a single dose or divided into several doses.

The present disclosure will be further described by way of the following examples. However, it should be understood that the following examples are intended solely for the purpose of illustration and should not be construed as limiting the present disclosure in practice.

EXAMPLES

General Experimental Materials:

1. *Lactobacillus plantarum* CGMCC No. 13008

*Lactobacillus plantarum* CGMCC No. 13008 (also known as *Lactobacillus plantarum* TWK10) used in the following example has been deposited at the China General Microbiological Culture Collection Center (CGMCC) since Sep. 13, 2016 according to the Budapest Treaty, and is available to the public.

In addition, *Lactobacillus plantarum* TWK10 has been deposited at the Bioresource Collection and Research Center (BCRC) of the Food Industry Research and Development institute (FIRDI) (No. 331, Shih-Pin Rd., Hsinchu City 300, Taiwan) under a deposit number BCRC 910734 since Jun. 30, 2016, and is available to the public.

2. Experimental Animal

Wistar rats (6 weeks old, weighing approximately 200 to 260 g) used in the following example were purchased from BioLasco Taiwan Co., Ltd. All experimental animals were housed in an animal room with an independent air conditioning system with an alternating 12-hour light and 12-hour dark cycle, a room temperature maintained at 21±2° C., a relative humidity maintained at 55110%, and with water and feed adequately supplied. All experimental procedures involving the experimental animals were approved by the Institutional Animal Care and Use Committee (IACUC) of Fu Jen Catholic University, and were carried out in accordance with the Guide for the Care and Use of Laboratory Animals of the National Institutes of Health, USA.

3. Bioceramic Implant

The bioceramic implant used for bone implantation in the following example was provided by Professor Huang Yu-Tzu's laboratory at the School of Medicine, Fu Jen Catholic University. The bioceramic implant was made from a silica-based bioceramic scaffold that was prepared by mixing silica powder (Nippon Light Metal Holdings Company, Ltd.) and silica gel (Nissan Chemical America Corporation), with reference to TW I421062 B using 3D printing technology.

General Procedures:

1. Statistical Analysis

In the following example, the experimental data of each group are expressed as mean±standard error (SE), and were analyzed using Mann-Whitney U test to assess differences between the groups. Statistical significance is indicated if the result of statistical analysis is p<0.05.

Example 1. Evaluation of Efficacy of *Lactobacillus plantarum* TWK10 in Promotion of Bone Healing Experimental Method:

A. Preparation of Freeze-Dried Bacterial Powder of *Lactobacillus plantarum* TWK10

First, *Lactobacillus plantarum*. TWK10 was inoculated into MRS medium, and cultured at 37° C. for 16 to 18 hours. Thereafter, the resulting culture was centrifuged at 5000 rpm for 10 minutes at 4° C. Then, the supernatant was removed, and the pellets were washed with an appropriate amount of physiological saline. A freeze-drying treatment was carried out after performing bacterial count using a plate counting medium, followed by mixing with an appropriate amount of maltodextrin, thereby obtaining a freeze-dried bacterial powder of *Lactobacillus plantarum* TWK10 having a bacterial concentration of $10^{10}$ CFU/g.

B. Administration of *Lactobacillus plantarum* TWK10 and bone transplantation First, the Wistar rats were randomly divided into 4 groups (n=4 in each group), namely, two control groups (i.e., control group 1 and control group 2) and two experimental groups (i.e., experimental group 1 and experimental group 2). Next, via oral gavage, the rats in each of the experimental groups were administered with the freeze-dried bacterial powder of *Lactobacillus plantarum* TWK10 obtained in Item A above at a dosage of $10^9$ CFU/kg (in ddH$_2$O), while the rats in each of the control groups were administered with an equal weight of maltodextrin (in ddH$_2$O), in which the rats in the control group 1 and experimental group 1 were administered 5 times a week for a total time period of 5 weeks, whereas the rats in the control group 2 and experimental group 2 were administered twice a week for a total time period of 13 weeks.

At the end of the first week after start of administration, the rats in each group were subjected to bone destruction and bone transplantation described hereinafter. First, the rats in each group were anesthetized by inhaling isoflurane. Next, the leg abdomen of the rat in each group was shaved, and then the skin layer was cut using a sterile surgical scissor to form an incision, followed by using a sterile scalpel to dissect the muscle beneath the skin layer such that the femur beneath the muscle was exposed. After that, the femur was subjected to bone destruction using a drill, so that a bore hole having a diameter of 2 mm is formed in the femur. Finally, a bioceramic implant is implanted into the bore hole, and suture is performed.

At the end of the fifth week after start of administration, the rats in the control group 1 and experimental group 1 were sacrificed using CO$_2$, and then the femurs were removed to be subjected to the experiments in the following items C to E. In addition, at the end of the thirteenth week after start of administration, the rats in the control group 2 and experimental group 2 were sacrificed in a similar manner using CO$_2$, and then the femurs were removed to be subjected to the experiments in the following items C to E.

C. Analysis of Bone Quality Parameters

The femurs of the rats were photographed using a micro-computed tomography (micro-CT) system (=SCAN 1176, Bruker Corporation) at a magnification of 400×, and then five regions surrounding the implantation of the bioceramic implant were randomly selected to measure bone volume (BV), tissue volume (TV), and bone mass density (BMD) (g/mm$^3$).

Bone value fraction (BV/TV) (%) was calculated by substituting the measured bone volume and tissue volume into the following formula (1):

$$A = (B/C) \times 100 \tag{1}$$

wherein: A=bone value fraction (BV/TV) (%)

B=bone volume (mm$^3$)

C=tissue volume (mm$^3$)

Thereafter, the experimental data thus obtained were analyzed according to the procedures as described in Item 1 "Statistical Analysis" of the General Procedures.

D. Histopathological Analysis

The femurs of the rats were subjected to fixation overnight using 10% formaldehyde solution, followed by decalcification using 3% hydrochloric acid for 5 hours. Next, the thus fixed and calcified femurs were embedded in paraffin, followed by sectioning, thereby obtaining tissue sections having a thickness of 4 µm.

After that, a portion of the tissue sections was stained using hematoxylin-eosin according to techniques well-known and customary to those skilled in the art. The thus stained tissue sections were observed and photographed using an optical microscope (Olympus BX51, Japan) at a magnification of 400×, followed by counting the numbers of active osteoblast and inactive osteoblast, respectively. The active osteoblast ratio (I) was calculated by substituting the thus obtained number of active osteoblasts and number of inactive osteoblasts into the following formula (2):

$$D = [E/(E + F)] \times 100 \tag{2}$$

wherein: D=active osteoblast ratio (3)

E=number of active osteoblasts

F=number of inactive osteoblasts

In addition, lamellar bone formation was observed and photographed under polarized light view, and analyzed using ImageJ Imaging Software (version 1.48), so as to measure the lamellar bone area and total tissue area surrounding the implantation of the bioceramic implant, wherein the formation of lamellar bone represents the occurrence of bone maturation. The lamellar bone area percentage was calculated by substituting the thus measured lamellar bone area and total tissue area into the following formula (3):

$$G = (H/I) \times 100 \qquad (3)$$

wherein: G=lamellar bone area percentage (3)

H=lamellar bone area (mm²)

I=total tissue area (mm²)

Thereafter, the experimental data thus obtained were analyzed according to the procedures as described in Item 1 "Statistical Analysis" of the General Procedures.

E. Immunohistochemistry Stain

Another portion of the tissue sections obtained in Item D above was collected, and then immunohistochemistry stain was performed using anti-special AT-rich sequence-binding protein 2 (SATB2) antibody (Manufacturer: Abcam; Catalogue no.: ab92446) as a primary antibody, and Rabbit specific HRP/DAB (ABC) Detection IHC Kit (Manufacturer: Abcam; Catalogue no.: ab64261) according to techniques well-known and customary to those skilled in the art. The thus stained tissue sections were observed and photographed using the optical microscope (Olympus BX51, Japan) at a magnification of 400×, followed by analysis using ImageJ Imaging Software (version 1.48), so as to measure the tissue area with SATB2 expression and the total tissue area which surround the implantation of the bioceramic implant, wherein the expression of SATB2 represents a situation with osteoblastogenesis. The SATB2 expression percentage (%) was calculated by substituting the thus measured tissue area with SATB2 expression and total tissue area into the following formula (4):

$$J = (K/L) \times 100 \qquad (4)$$

wherein: J=SATB2 expression percentage (I)

K=tissue area with SATB2 expression (mm²)

L=total tissue area (mm²)

Thereafter, the experimental data thus obtained were analyzed according to the procedures as described in item 1 "Statistical Analysis" of the General Procedures.

Results:

A. Analysis of Bone Quality Parameters

Figure 2:
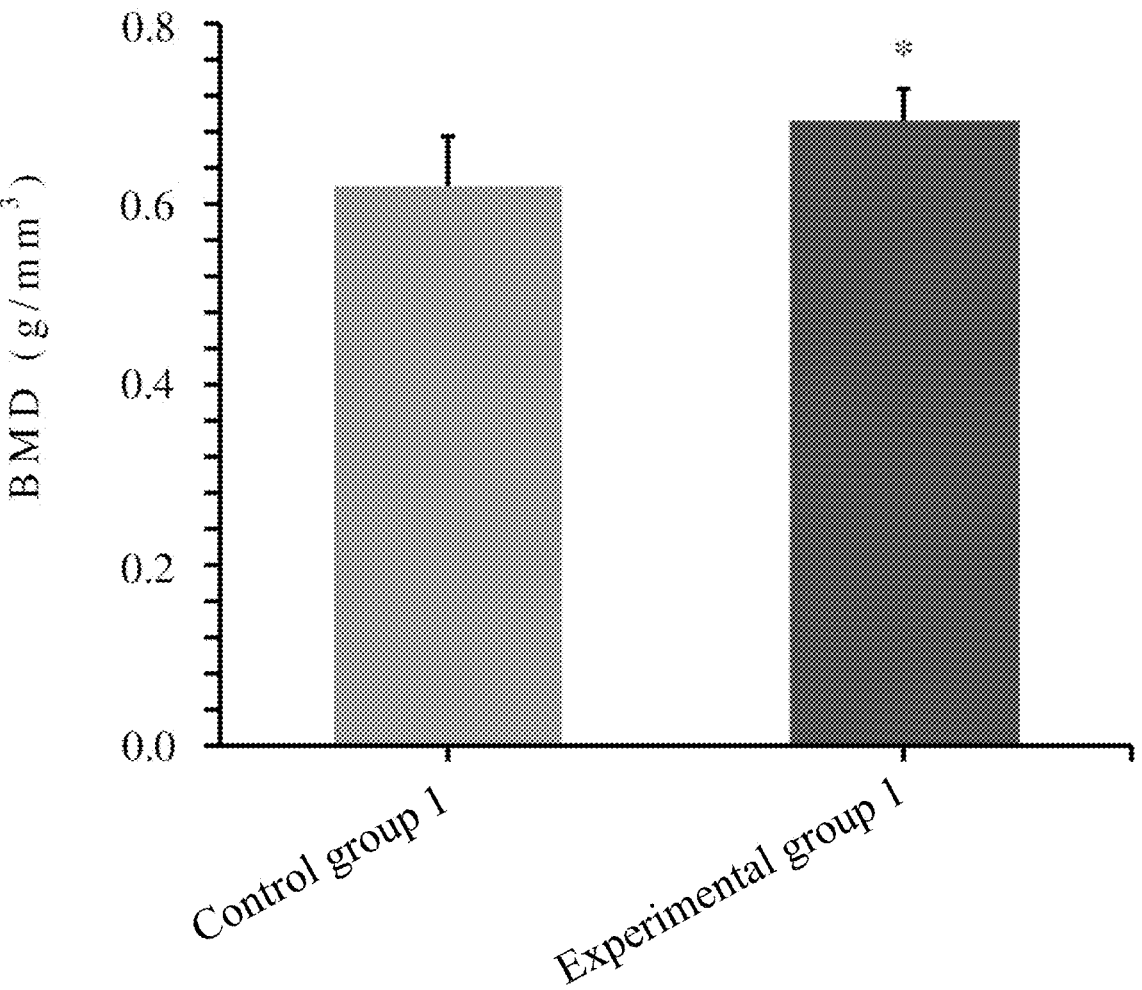

FIGS. 1 and 2 respectively show the BV/TV and BMD measured in the femurs of the rats in control group 1 and experimental group 1 at the end of the fifth week after start of administration. As shown in FIGS. 1 and 2, the BV/TV and BMD measured in the experimental group 1 increased significantly compared with those in the control group 1.

B. Histopathological Analysis

Figure 3:
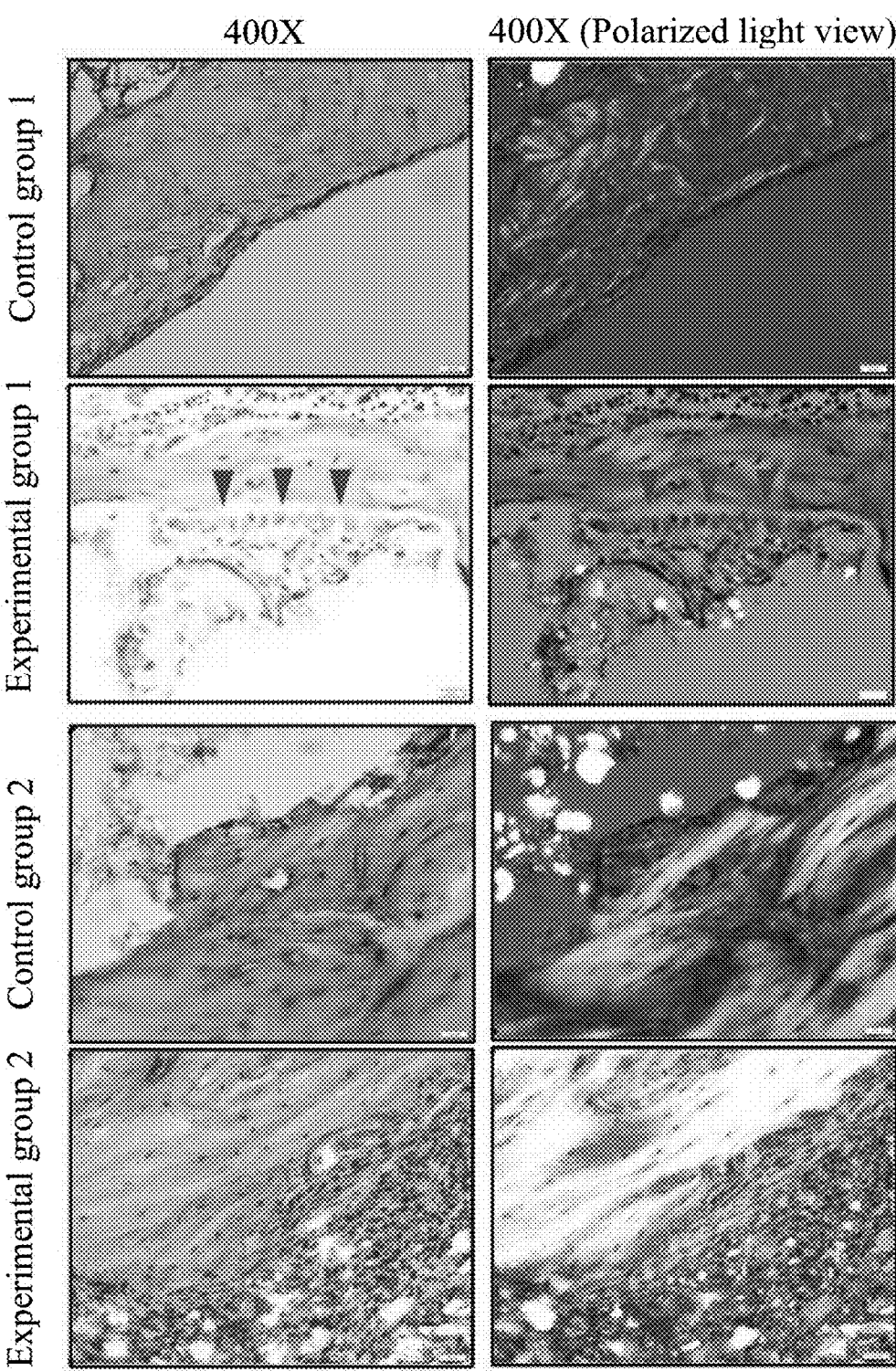
FIG. 3 shows the result of hematoxylin-eosin staining of femoral tissue sections of the rats in each group of Example 1, infra, in which the red arrows indicate osteoblasts.

FIG. 3 shows the results of hematoxylin-eosin staining of the femoral tissue sections of the rats in each group at the end of the fifth week or the thirteenth week after start of administration. As shown in FIG. 3, the femoral tissue of the experimental group 1 significantly has more osteoblasts compared with those of the control group 1, and the bones formed were thicker in the femoral tissue of the experimental group 2 compared with those of the control group 2.

Figure 4:
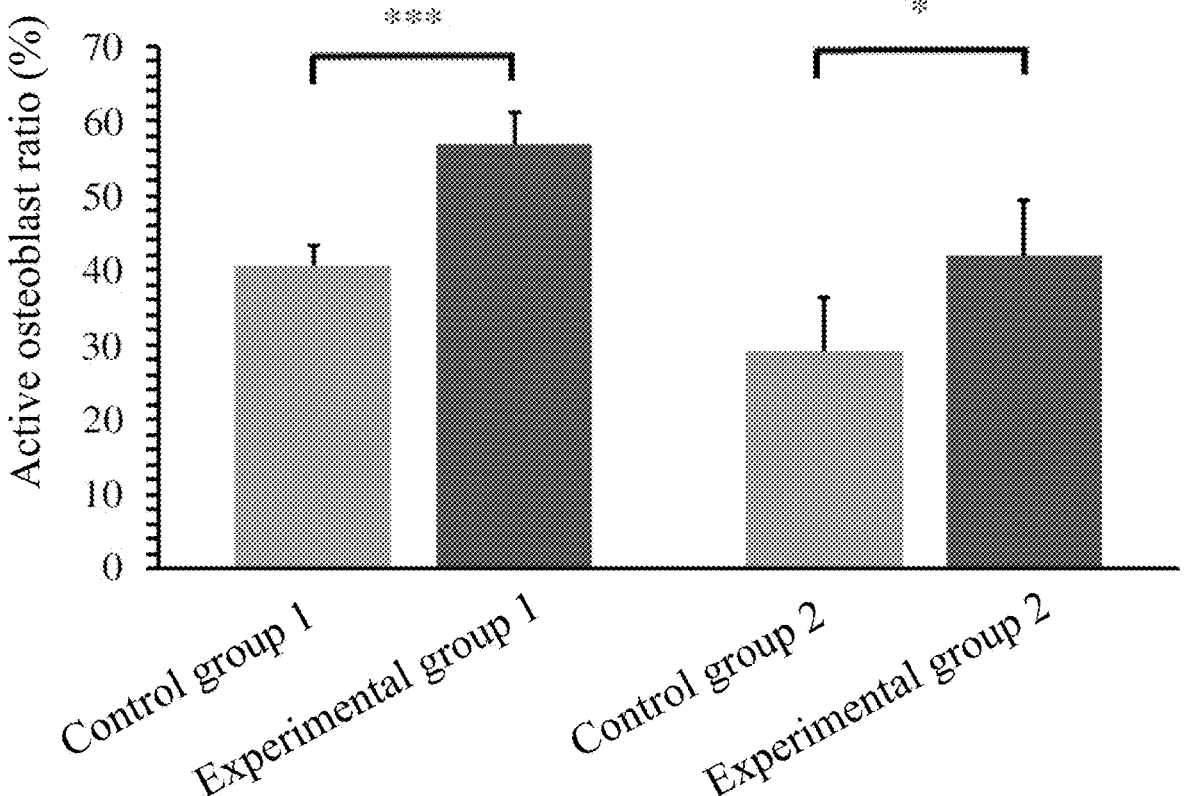
FIG. 4 shows the active osteoblast ratio (%) in the femoral tissue sections of the rats in each group of Example 1, infra, in which the symbols "*" and respectively represent p<0.05 and p<0.001 (compared with the corresponding control group)

FIG. 4 shows the active osteoblast ratio (%) measured in femoral tissue sections of the rats in each group at the end of the fifth week or the thirteenth week after start of administration. As shown in FIG. 4, the active osteoblast ratio measured in each of the experimental groups was significantly higher than that in the corresponding control group.

Figure 5:
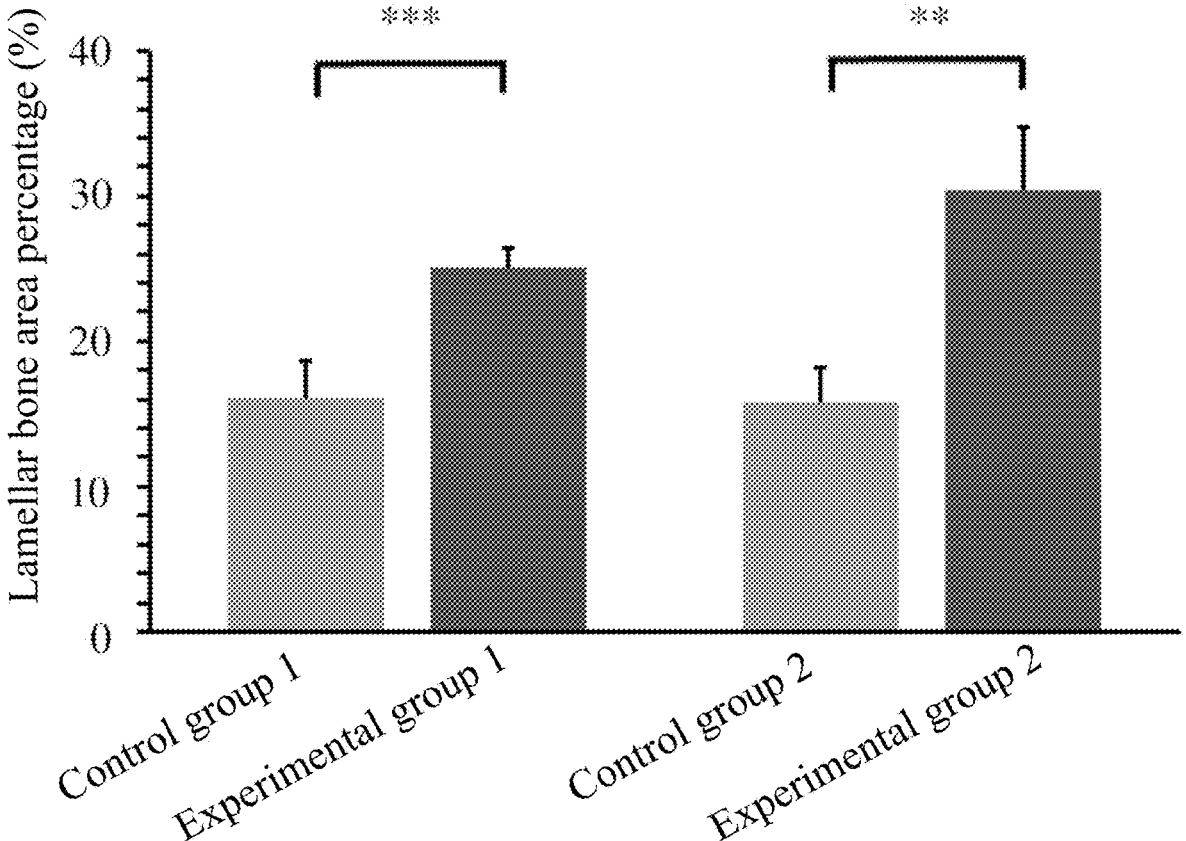
FIG. 5 shows the lamellar bone area percentage (%) in the femoral tissue sections of the rats in each group of Example 1, infra, in which the symbols "" and "*" respectively represent p<0.01 and p<0.001 (compared with the corresponding control group)

FIG. 5 shows the lamellar bone area percentage (%) measured in femoral tissue sections of the rats in each group at the end of the fifth week or the thirteenth week after start of administration. As shown in FIG. 5, the lamellar bone area percentage measured in each of the experimental groups was significantly higher than that in the corresponding control group.

C. Immunohistochemistry Stain

Figure 6:
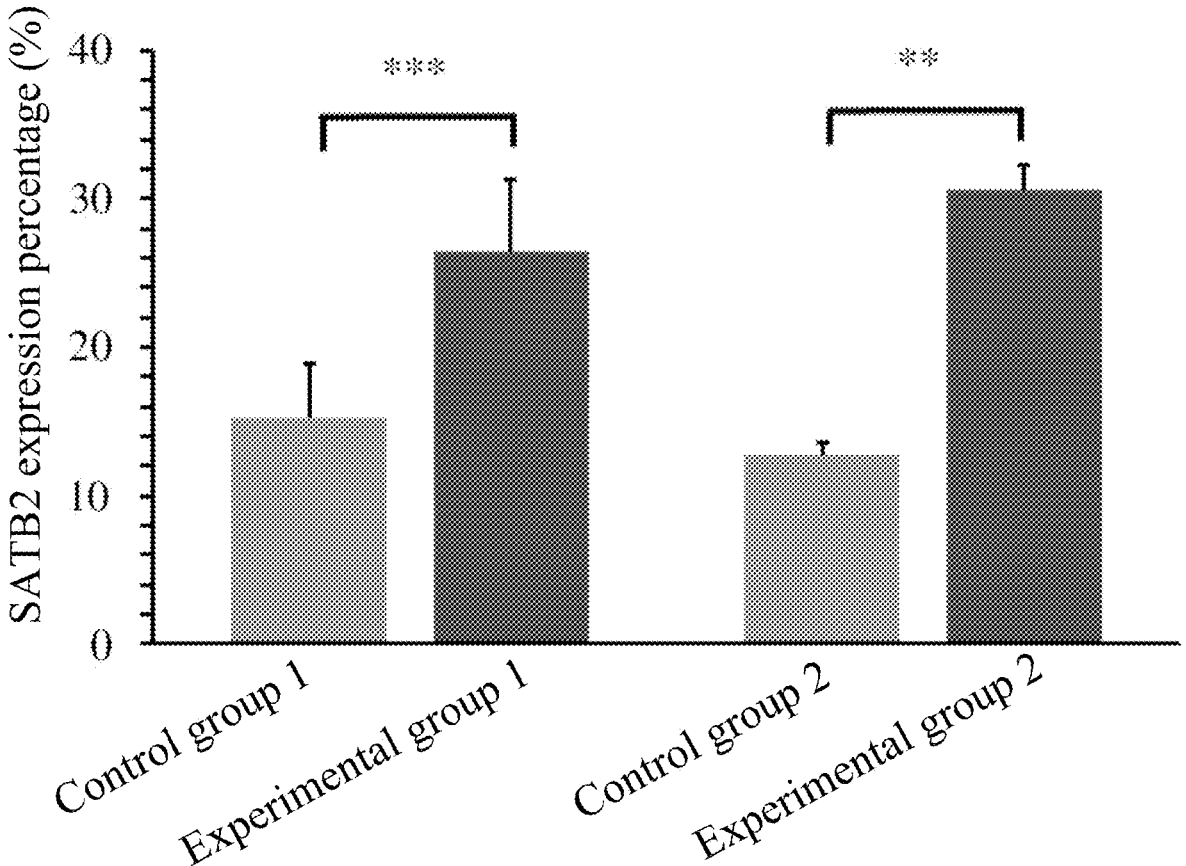
FIG. 6 shows the SATB2 expression percentage (%) in the femoral tissue sections of the rats in each group of Example 1, infra, in which the symbols "" and "*" respectively represent p<0.01 and p<0.001 (compared with the corresponding control group).

FIG. 6 shows the SATB2 expression percentage measured in femoral tissue sections of the rats in each group at the end of the fifth week or the thirteenth week after start of administration. As shown in FIG. 6, the SATB2 expression percentage measured in each of the experimental groups was significantly higher than that in the corresponding control group.

In summary, the experimental results above demonstrate that, *Lactobacillus plantarum* TWK10, whether administered for 5 weeks or thirteen weeks, can effectively promote the activation and generation of osteoblasts, and bone maturation, and thus, the applicants believe that *Lactobacillus plantarum* TWK10 has a great potential for promoting bone healing.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A method for promoting bone healing in a subject, comprising administering to the subject in need thereof a composition including *Lactobacillus plantarum* TWK10 deposited at China General Microbiological Culture Collection Center with an accession number CGMCC No. 13008.

2. The method according to claim 1, wherein the composition is a food product or a pharmaceutical composition.

3. The method according to claim 2, wherein the pharmaceutical composition is in a dosage form for oral administration, parenteral administration or topical administration.

* * * * *